(12) United States Patent
Chen et al.

(10) Patent No.: US 8,927,196 B2
(45) Date of Patent: Jan. 6, 2015

(54) METHOD OF MAKING AN (ALKYL)ACRYLOYL POLYCARBONATE

(75) Inventors: Wei Chen, Suzhou (CN); Fenghua Meng, Suzhou (CN); Rong Wang, Suzhou (CN); Ru Cheng, Suzhou (CN); Zhiyuan Zhong, Suzhou (CN)

(73) Assignee: SSENS B.V., Enschede (NL)

( * ) Notice: Subject to any disclaimer, the term of this patent is extended or adjusted under 35 U.S.C. 154(b) by 0 days.

(21) Appl. No.: 13/386,238

(22) PCT Filed: Dec. 4, 2009

(86) PCT No.: PCT/EP2009/008859
§ 371 (c)(1),
(2), (4) Date: Jul. 31, 2012

(87) PCT Pub. No.: WO2011/009478
PCT Pub. Date: Jan. 27, 2011

(65) Prior Publication Data
US 2012/0294845 A1 Nov. 22, 2012

(30) Foreign Application Priority Data
Jul. 23, 2009 (CN) .......................... 2009 1 0181912

(51) Int. Cl.
*C08G 63/02* (2006.01)
(52) U.S. Cl.
USPC .................. 430/287.1; 430/286.1; 430/281.1
(58) Field of Classification Search
USPC ................. 430/287.1, 286.1, 281.1
See application file for complete search history.

(56) References Cited
U.S. PATENT DOCUMENTS

| | | | | |
|---|---|---|---|---|
| 2,864,804 A * | 12/1958 | Shokal et al. | .................. | 525/386 |
| 3,301,825 A * | 1/1967 | Hostettler et al. | ............. | 528/354 |
| 6,194,124 B1 * | 2/2001 | Choi et al. | .................. | 430/287.1 |
| 6,503,991 B2 * | 1/2003 | Shalaby | ........................ | 525/437 |

FOREIGN PATENT DOCUMENTS

| | | | |
|---|---|---|---|
| CN | 101239966 | 8/2008 | |
| EP | 0687667 A1 * | 6/1995 | ............. C07C 69/96 |
| JP | 6279433 | 4/1994 | |

OTHER PUBLICATIONS

International Search Report and Written Opinion, Feb. 19, 2010, in PCT/EP 2009/008859.

* cited by examiner

*Primary Examiner* — David Lukton
(74) *Attorney, Agent, or Firm* — Cook Alex Ltd.

(57) ABSTRACT

The invention relates to a method for making a polymer wherein during the polymerization is incorporated in the polymer chain by ring opening polymerization a cyclic (alkyl)acryloyl carbonate having the formula (4): wherein $R_1$ and $R_2$ each independently are hydrogen, methyl or ethyl. Preferable the polymer is an (alkyl)acryloyl polycarbonate such that at least one first monomer a cyclic (alkyl)acryloyl carbonate having the formula (4). The (alkyl)acryloyl polyester may be modified and used in biodevices.

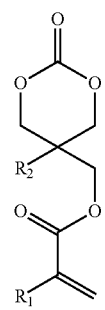

(4)

4 Claims, 5 Drawing Sheets

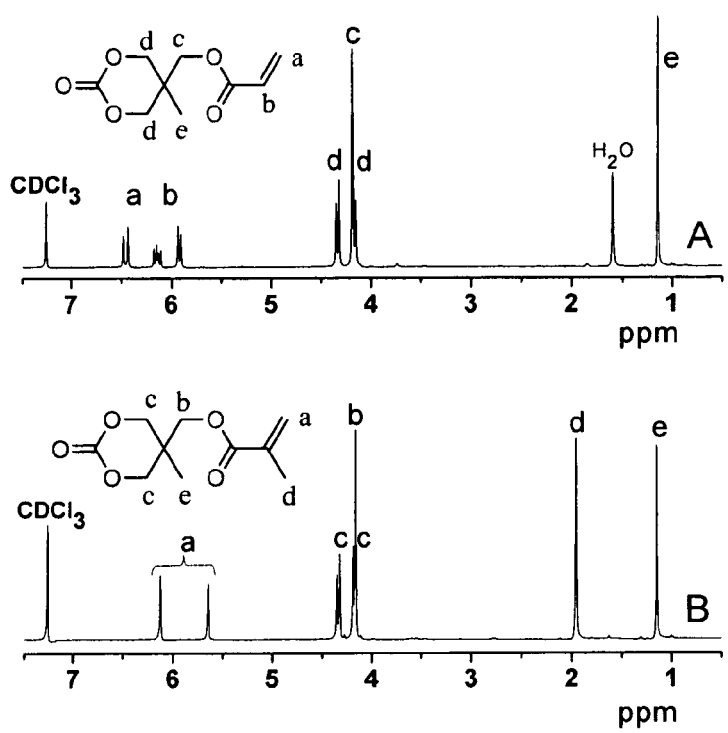
Figure 1. $^1$H NMR spectra (400 MHz, CDCl$_3$) of AC (A) and MAC (B) monomers.

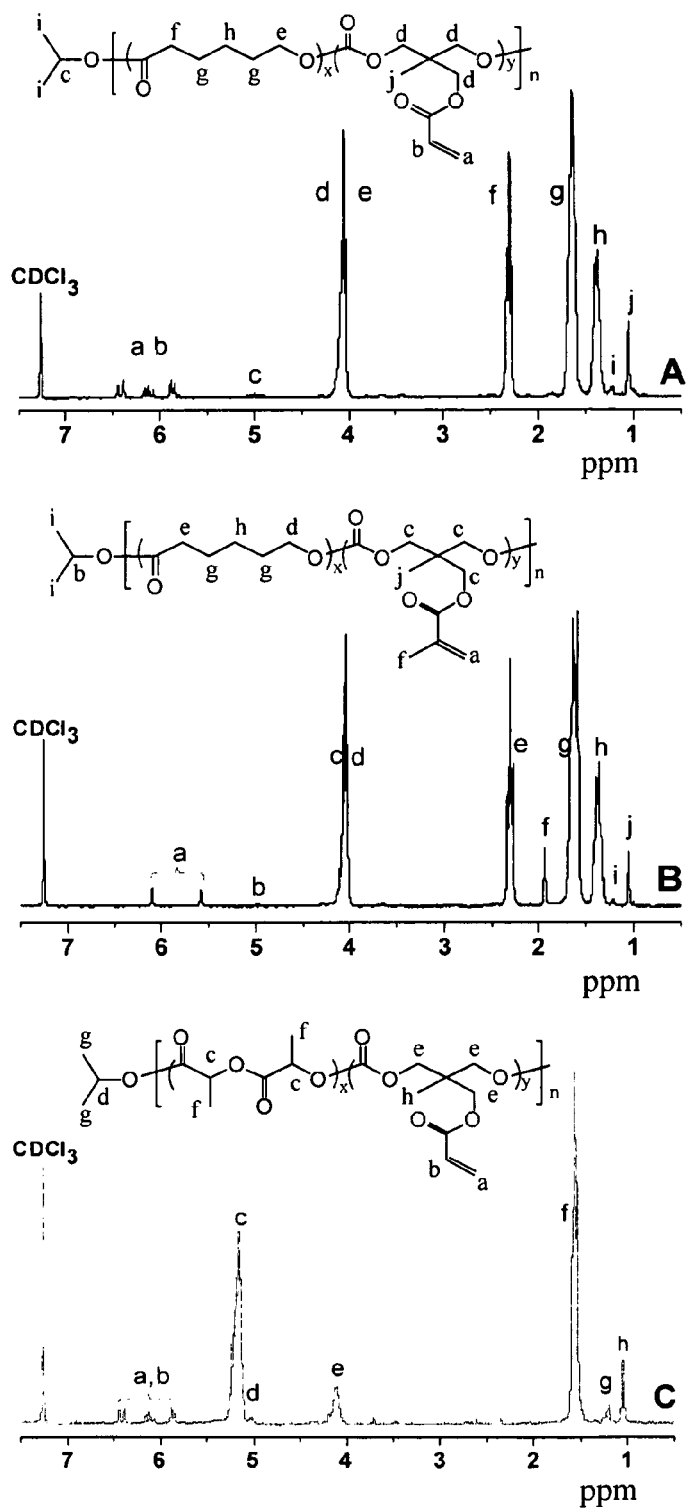
Figure 2. $^1$H NMR spectra (300 MHz, CDCl$_3$) of (M)AC copolymers. (A) P(CL-co-AC); (B) P(CL-co-MAC); and (C) P(LA-co-AC).

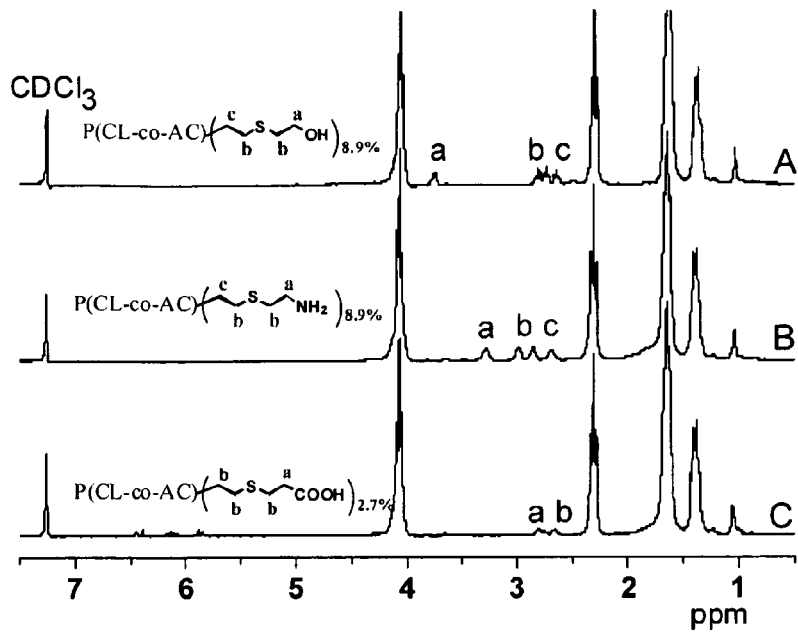
Figure 3. $^1$H NMR spectra (300 MHz, CDCl$_3$) of P(CL-co-AC) 8.9% copolymer modified with 2-mercapitoethanol (A), 2-mercaptoethylamine (B), and 3-mercaptopropanoic acid (C).
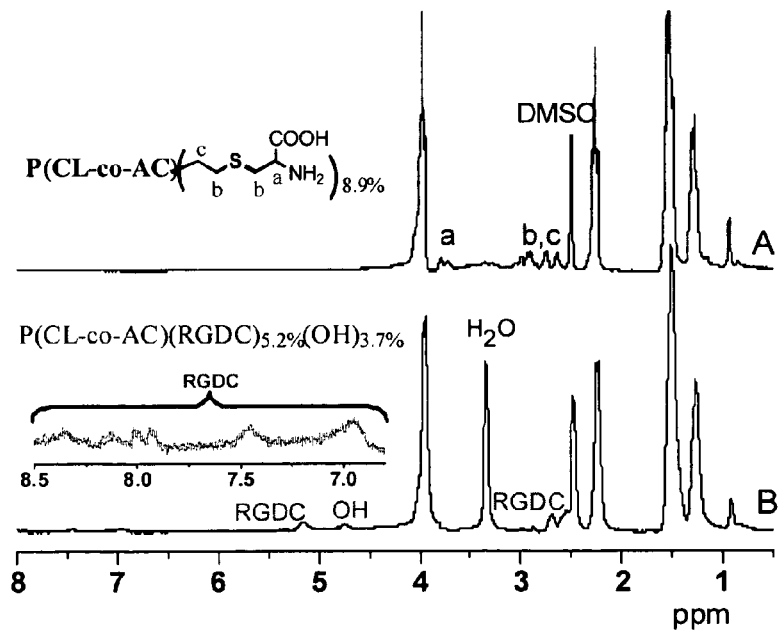
Figure 4. $^1$H NMR spectra (300 MHz, DMSO-$d_6$) of P(CL-co-AC) 8.9% copolymer modified with L-cysteine (A) and RGDC peptide (B).

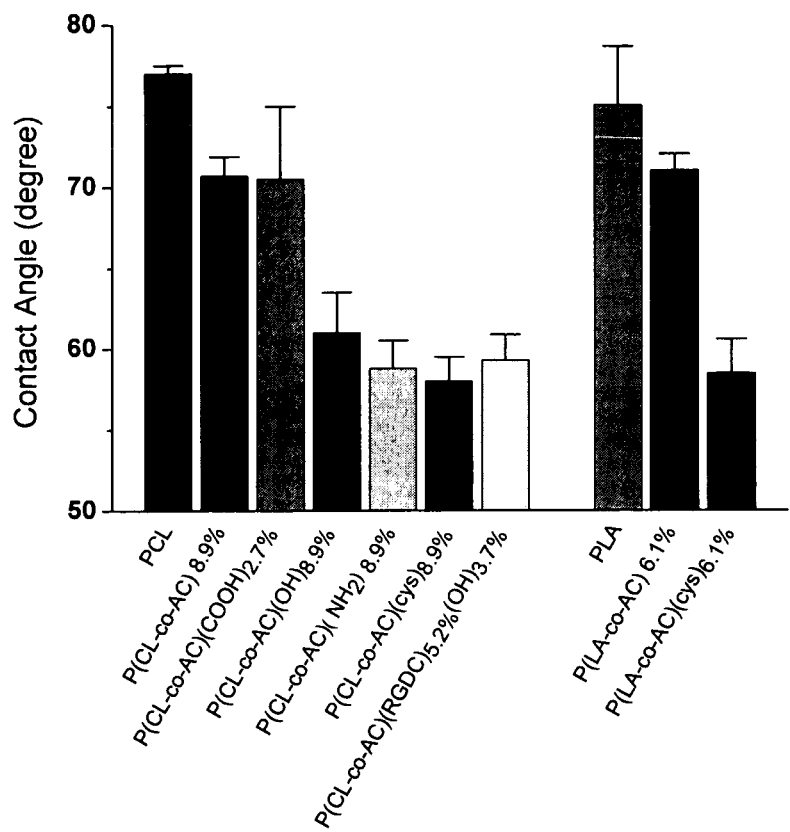
Figure 5. Contact angle measurements of functional copolymer films.

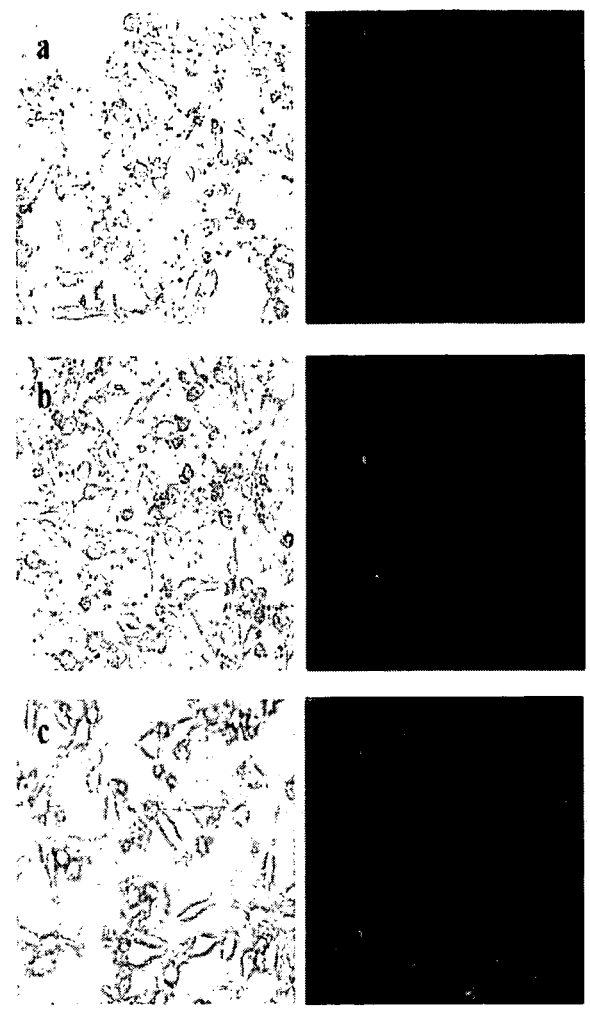
Figure 6. Images (×400) of L929 cells (left panel) and their nuclei stained with Hoechst 33258 (blue, right panel) after 3 day culture on film of P(CL-co-AC)(RGDC)$_{5.2\%}$(OH)$_{3.7\%}$ (a), film of P(CL-co-AC) (b); and tissue culture plastic (c).

METHOD OF MAKING AN (ALKYL)ACRYLOYL POLYCARBONATE

This application is a 371 of PCT/EP2009/008859, filed Dec. 4, 2009, which claims foreign priority to CN 200910181912.2, filed Jul. 23, 2009.

The present invention relates to a method of making a new polymer in which at least one (alkyl)acryloyl group is incorporated in the polymer chain by ring opening polymerisation of a cyclic (alkyl)acryloyl carbonate, such as new (alkyl) acryloyl polycarbonates, to the polymer and (alkyl)acryloyl polycarbonates obtainable by this method, to biodevices which comprise or have been made using the polymer or (alkyl)acryloyl polycarbonates, and to the cyclic (alkyl)acryloyl carbonate.

In the biomedical technology there is a need for polymers that can be used under biological conditions and are preferably also biodegradable. Such polymers are to be modified such that bioactive molecules can be bound directly or indirectly to the polymer. The polymer with the bioactive molecule bound thereto may be used as such or may be attached to a biosupport, such as a stent, an implant, a blood vessel, a cell compartment, a pharmaceutical device, a hydrogel or the like. The modification of the polymers may be by fuctionalization, crosslinking and/or grafting. The crosslinking and grafting may take place before or after functionalization, but may also (in addition) be carried out before or after bonding to the biosupport.

Aliphatic polyesters and polycarbonates, such as poly(ε-caprolactone) (PCL), polylactide (PLA), poly(lactide-co-glycolide) (PLGA), and poly(trimethylene carbonate) (PTMC), are important synthetic biodegradable materials. These polymers are biocompatible, have suitable mechanical properties, are degradable in vivo into non-toxic products, and readily processable to fibers, films, rods, microparticles, nanoparticles, and porous three-dimensional constructs. In addition to applications as resorbable sutures and in various medical devices, degradable polyesters and polycarbonates are one of the key biomaterials used and/or currently investigated for controlled drug delivery, tissue engineering and regenerative medicine.

These degradable polymers are, nevertheless, not ideal. In practice, very often they cannot meet requirements of various biological applications, due to their high hydrophobicity, improper degradation profile, and/or lack of reactive centers in the polymer chain for chemical modification. While in the ever advancing biomedical technology there is a need for the development of complex biologically active biomaterials. In the prior art have been described inter alia functional aliphatic polyesters and polycarbonates containing pendant groups, such as e.g. hydroxyl (Leemhuis, M., et al, Macromolecules 2006, 39 (10), 3500-3508), carboxyl (in't Veld, P. J. A., et al, Makromolek. Chem. 1992, 193 (11), 2713-2730), and amine (Zhou, Y., et al, Macromol. Rapid Commun. 2005, 26 (16), 1309-1314). These functional polymers on one hand show improved physiochemical properties such as enhanced hydrophilicity and biodegradability, and on the other hand facilitate drug conjugation or further derivatization. Their synthesis is, however, usually a multi-step process involving protection and deprotection of the functional groups before and after the polymerization, which may result in low overall yields as well as degradation.

Notably, there are several reports on degradable polymers presenting functional groups, such as acryloyl (such as Mecerreyes, D. et al., Macromol. Rapid Comm. 2000, 21, 779-784; Vaida, C. et al., J. Polym. Sci. Polym. Chem. 2008, 46 (20), 6789-6800), allyl (such as Pratt, R. C., et al, Chem. Comm. 2008, (1), 114-116), or alkyne/azide (such as Lu, C. H., et al, J. Polym. Sci. Polym. Chem. 2007, 45 (15), 3204-3217; Riva, R. et al., Macromolecules 2007, 40, 796-803). In these processes no protection/deprotection steps are needed and they can readily be transformed into diverse functionalities through post-polymerization modification. In particular, functional PCL containing acryloyl groups appears to be of interest in that (1) further derivatization through the Michael addition chemistry with thiol-containing molecules is highly selective and is tolerant to a variety of functional groups including hydroxyl, carboxyl, and amine; (2) reaction takes place under very mild conditions, so degradation is minimized; and (3) no catalyst is needed and no side products would apparently be produced, thereby precluding possible contaminations. Nevertheless, it has been reported (see Vaida, C. et al, Macromol. Symp. 2008, 272, 28-38), that polymerization of γ-acryloyl-ε-caprolactone (ACL) is associated with significant side reactions. The other drawback is that ACL is not able to copolymerize with lactide (LA) monomers. When needed the (co)polymer may be grafted with unsaturated monomers.

The present invention has for its object to provide a method for making functional, and preferably biodegradable polymers having incorporated in the polymer chain, such as by ring opening polymerization, novel cyclic carbonate monomers, namely acryloyl carbonate (AC) and (alkyl)acryloyl carbonate (AAC), in particular (meth)acryloyl carbonate (MAC). The polymers such as (alkyl)acryloyl polycarbonates are prepared by ring opening polymerization. Preferably these polymers, in particular the polycarbonates, may be modified. This modification takes place at the pendant (alkyl) acryloyl groups, and comprise functionalization, crosslinking and/or grafting in any desired order. For the functionalization use can be made of the Michael addition reaction.

The AC, AAC and MAC monomers can be readily synthesized and copolymerized with a variety of different comonomers, such as cyclic alkylesters, cyclic diesters, morpholinediones, dioxanones, and cyclic alkylcarbonates. The copolymerization may take the form of a block polymerization. The copolymer obtained comprises one or more blocks of the at least one first monomer and/or the at least one comonomer. In addition, dependent of the function and/or on the properties desired the (co)polymer may be crosslinked by any suitable method.

The versatile post-polymerization modifications of the (co) polymers of the invention yield a range of modified biocompatible materials. The combination of ring opening polymerisation and modification by Michael addition chemistry has shown to be an efficient and practical approach to develop biologically active biomaterials.

The polymerization method according to the invention may be a polymerisation in which at least one cyclic (alkyl) acryloyl carbonate is incorporated in the polymer chain by ring opening polymerization, a homopolymerisation of one cyclic (alkyl)acryloyl carbonate, a copolymerisation of two or more cyclic (alkyl)acryloyl carbonates, or a copolymerisation of at least one cyclic (alkyl)acryloyl carbonate and at least one second comonomer. These second comonomers may be selected from the group comprising cyclic alkylesters, cyclic diesters, morpholinediones, dioxanones, and cyclic alkylcarbonates.

The cyclic (alkyl)acryloyl carbonate may be produced directly or indirectly from the corresponding triols. In a first method according to the invention is the cyclic (alkyl)acryloyl carbonate formed from the triol 1,1,1-tris(hydroxyl methyl) $C_1$-$C_3$alkane. Preferred are in particular 1,1,1-tris (hydroxyl methyl)ethane and 1,1,1-tris(hydroxyl methyl) propane as they are readily available.

Following the direct synthesis the triol is reacted with (alkyl)acryloyl chloride. The mono-(alkyl)acryloyl derivative formed is reacted with an alkyl chloroformate, in particular ethyl chloroformate. This results in the cyclic (alkyl)acryloyl carbonate with formula (4)

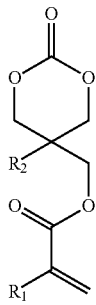

(4)

wherein $R_1$ and $R_2$ are each independently hydrogen, methyl or ethyl. If required the cyclic (alkyl)acryloyl carbonate obtained is purified, such as by crystallisation.

Following the indirect synthesis, the triol is first protected by forming an arylidene acetal with two of the three hydroxyl groups. For instance arylidene acetal is a benzylidene acetal (1), see scheme 1. This benzylidene acetal is reacted with (alkyl)acryloyl chloride forming a mono-(alkyl)acryloyl derivative (3). Subsequently, cyclization is performed by reaction with an alkyl chloroformate, in particular ethyl chloroformate. This results in the same cyclic (alkyl)acryloyl carbonate with formula (4) as in the direct synthesis.

In summary, it may be preferred that the cyclic (alkyl) acryloyl carbonate is prepared by (i) (alkyl)acrylation of 1,1, 1-tris(hydroxyl methyl)alkane or (ii) (alkyl)acrylation of aryl acetal protected 1,1,1-tris(hydroxyl methyl)alkane, deprotection, and ring-formation. This (alkyl)acrylation is for instance an acrylation, a methacrylation, or an ethylacrylation.

The cyclic (alkyl)acryloyl carbonate with formula (4) can be used for incorporation in a polymer chain by ring opening polymerization, preferably as the first monomer in a homopolymerisation for making the (alkyl)acryloyl polycarbonates according to the invention. Obviously, two or more different cyclic (alkyl)acryloyl carbonates, such as cyclic acryloyl carbonate, cyclic (meth)acryloyl carbonate and (ethyl)acryloyl carbonate can be used for making (alkyl)acryloyl polycarbonates of the invention. This polymerisation includes or proceeds via a ring-opening polymerisation preferably in the presence of a catalyst, such as stannous octoate or zinc bis[bis(trimethylsilyl)amide]. Often a polymerisation initiator is used, such as methoxy PEG, or an alkanol, e.g., isopropanol.

These polymers can be produced with a controlled molecular weight and a desired polydispersity (PDI). The polymers of the present invention have generally a number average molecular weight $M_n$ of about 500 to 1,000,000, such as 1000 to 500,000 or 1000 to 50,000. The molecular weight $M_n$ may be determined by $^1$H NMR or by GPC. The PDI is generally in the range of 1.0 to 4.0 such as in the range of 1.0 to 2.0, like 1.12 to 1.80.

Thus, according to a first aspect of the invention is provided a method for making a polymer wherein during the polymerisation at least one (alkyl)acryloyl group is incorporated in the polymer chain by ring opening polymerisation a cyclic (alkyl) acryloyl carbonate having the formula (4):

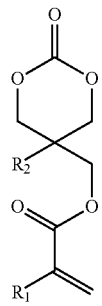

(4)

wherein $R_1$ and $R_2$ each independently are hydrogen, methyl or ethyl. The polymer obtained comprises in the polymer chain at least one pendant (alkyl)acryloyl group available for modification.

In a preferred embodiment the method for making an (alkyl)acryloyl polyester comprising the steps of:
i. providing at least one first monomer a cyclic (alkyl) acryloyl carbonate having the formula (4):

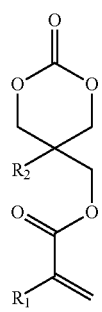

(4)

wherein $R_1$ and $R_2$ each independently are hydrogen, methyl or ethyl, and
ii. polymerising the at least first monomer and optionally with the second monomer thereby making (alkyl)acryloyl functionalized polycarbonate.

According to an embodiment the present invention also provides copolymers based on the (alkyl)acryloyl polycarbonates. Thereto, the above defined at least one first monomer, cyclic (alkyl)acryloyl carbonate having the formula (4), is copolymerized with at least one second monomer. This second monomer participates in the ring-opening polymerisation. Dependent on the type of second monomer used the (alkyl)acryloyl polycarbonate formed is an (alkyl)acryloyl polycarbonate, an (alkyl)acryloyl polyester carbonate, an (alkyl)acryloyl polyamide carbonate, or an (alkyl)acryloyl polyester amide carbonate. As desired the mol % of the second monomer can be adjusted dependent on the properties of the copolymer. The mol % may vary between 0.01 to 99.99 mol %, generally between 0.1 to 50 mol %, such as 0.5 to 20 mol %, like 1 to 15 mol %.

These properties are generally dictated by the ultimate use of the copolymer. For instance, by the introduction of carbonate or amide carbonate groups in the polymer chain the copolymer becomes biodegradable to an extent dependent on the concentration of the biodegradable groups in the polymer chain.

Obviously, the produced copolymers may comprise one or more blocks of each of the monomers participating in the polymerization. In addition, the copolymers may be modified, such as functionalized, crosslinked, and/or grafted as described above in relation to the other (alkyl)acryloyl polycarbonates according to the invention.

According to a first example as a second monomer can be used a cyclic $C_3$-$C_{14}$-alkylester having the formula (5)

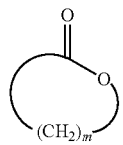

(5)

wherein m=3-14.

The copolymers formed may have the following structure (10):

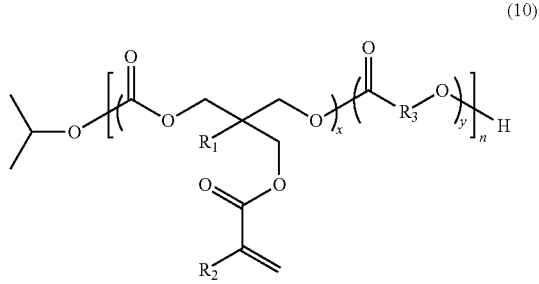

(10)

wherein $R_1$ and $R_2$ have the above identified meaning given in relation to formula (4). In the formula relate x and y to the mol % of the various monomers, and n an integer, relates to the number of repeating units. The values for x, y and n are dependent on the polymerisation conditions, the relative amounts of the first monomer and of the second monomer, and whether blocks of varying length have been used in the copolymerisation. Thus, both x and y may vary between for instance 0.01 and 99.99 mol %, such as 0.5 and 99.5 mol %. Furthermore, n may be within the range of 5 to 100,000, for instance 10-50,000, such as 100-1000. The meaning of $R_3$ is dependent on m. Thus $R_3$ represents $(CH_2)_m$ with m=3-14. Preferably m is 4, 5 or 14. Examples of suitable cyclic alkylesters are δ-valerolactone, ε-caprolactone (ε-CL) and ω-pentadecalactone.

According to a second example as the second monomer can be used a cyclic diester, having the formula (6)

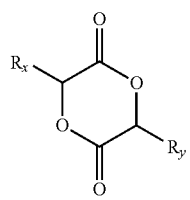

(6)

wherein $R_x$ and $R_y$ each independently are hydrogen, methyl or ethyl. A very practical example is lactide, wherein $R_x$ and $R_y$ are both methyl. In case of lactide the copolymer has the following structure (10):

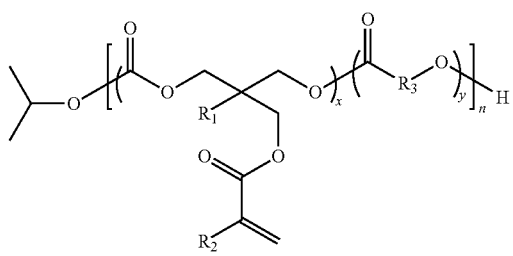

(10)

wherein $R_1$ and $R_2$ have the above identified meaning given in relation to formula (4) and $R_3$ has the formula (II)

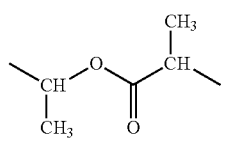

(11)

The (alkyl)acryloyl polycarbonate of the invention is a (alkyl)acryloyl polyester carbonate comprising next to carbonate groups also ester groups in the polymer chain. This will provide the (alkyl)acryloyl polyester carbonate of the invention with unique properties in relation to stability, biodegradation and biocompatibility.

As discussed in relation to the copolymer used as the second monomer the cyclic alkylester of formula (5), the values for x, y and n may be selected as required by the desired properties and are dependent on the polymerisation conditions, the relative amounts of the first monomer and of the second monomer, monomer-to-initiator ratios, and whether blocks of varying length have been used in the copolymerisation. Thus, both x and y may vary as indicated above.

According to a third example, as the second monomer can be used a morpholinedione having the formula (7)

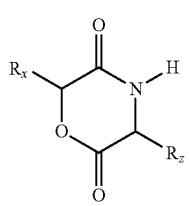

(7)

wherein $R_x$ is hydrogen, methyl or ethyl and independently $R_z$ is hydrogen, methyl, ethyl, or an amino acid residue which residue is optionally protected. The amino acid residue may originate from any amino acid, such the natural amino acids like glycine, valine, serine, cystein, proline, phenylalanine. The amino acid residue may be (temporarily) protected, such as in the form of a benzyl ester.

The resulting copolymer has the following structure (10):

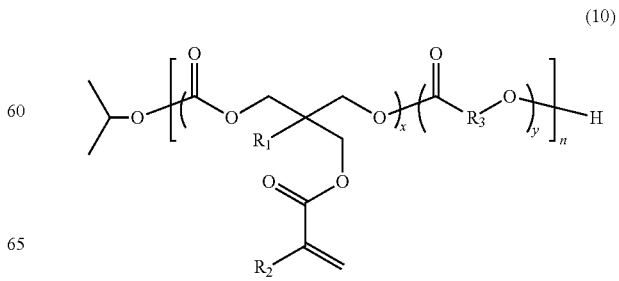

(10)

wherein $R_1$ and $R_2$ have the above identified meaning given in relation to formula (4) and $R_3$ has the formula (12)

$$—C(R_z)—NH—CO—C(R_x)— \qquad (12)$$

The (alkyl)acryloyl polycarbonate of the invention is a (alkyl) acryloyl polyester amide carbonate comprising next to carbonate groups, amide groups and ester groups in the polymer chain. This will provide the (alkyl)acryloyl polyester amide carbonate of the invention with unique properties in relation to stability, biodegradation and biocompatibility. Properties can be adjusted by proper selection of the values for x, y, n, $R_x$, and $R_z$.

According to a fourth example, as the second monomer can be used a dioxanone having the formula (8)

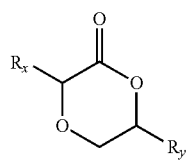
(8)

wherein $R_x$ and $R_y$ each independently are hydrogen, methyl or ethyl.

The resulting copolymer has the following structure (10):

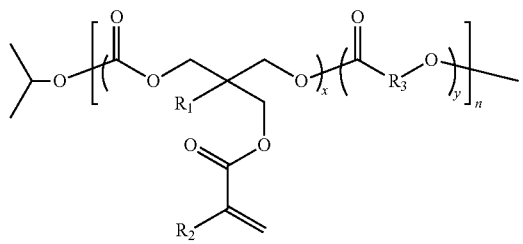
(10)

wherein $R_1$ and $R_2$ have the above identified meaning given in relation to formula (4) and $R_3$ has the formula (13)

$$—C(R_x)—O—CH_2—C(R_y)— \qquad (13)$$

The (alkyl)acryloyl polycarbonate of the invention is a (alkyl)acryloyl polyester carbonate comprising next to the carbonate groups also ester groups in the polymer chain. This will provide the (alkyl)acryloyl polyester carbonate of the invention with unique properties in relation to stability, biodegradation and biocompatibility. Properties can be adjusted by proper selection of the values for x, y, n, $R_x$, and $R_y$.

According to a fifth example, as a second monomer can be used a cyclic $C_3$-$C_5$-alkylcarbonate having the formula (9)

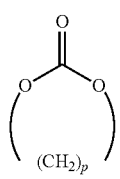
(9)

wherein p=3-5. Preferably p is 3 so that the cyclic alkylcarbonate is trimethylenecarbonate. The resulting copolymer has the following structure (10):

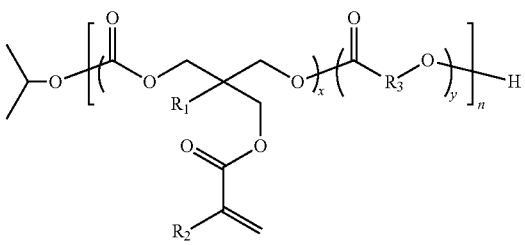
(10)

wherein $R_1$ and $R_2$ have the above identified meaning given in relation to formula (4) and $R_3$ has the formula (14)

$$—O—(CH_2)_p— \qquad (14)$$

The (alkyl)acryloyl polycarbonate of the invention is a (alkyl) acryloyl polycarbonate. This will provide the (alkyl)acryloyl polyester carbonate of the invention with unique properties in relation to stability, biodegradation and biocompatibility. Properties can be adjusted by proper selection of the values for x, y, n, and p.

Generally polymers, in particular the (alkyl)acryloyl polycarbonates according to the invention comprise a polymer chain in which by ring opening polymerisation is incorporated at least one cyclic (alkyl)acryloyl carbonate of formula (4), preferably a linear polymer chain formed by the cyclic (alkyl)acryloyl carbonates as the first monomers and optionally also by the second monomers. It is also possible that in view of the required properties and/or function of the polymer or (alkyl)acryloyl polycarbonate that the architecture of the polymer chain is adapted. According to the invention it is possible that the polymer chain is having a branched shape or star like shape. Thereto the polymerisation is performed with a multifunctional polymerisation initiator having a linear shape, branched shape, or star shape. According to a preferred embodiment the multifunctional polymerisation initiator is a multifunctional PEG having the required linear, branched or star shape.

The polymer or (alkyl)acryloyl polycarbonate comprises at least one unsaturated acryloyl group. The at least one unsaturated group may be used for modification, such as crosslinking, functionalization and/or grafting. In case of crosslinking are provided the cross linked polymer chains and/or (alkyl)acryloyl polymer chains, such as (alkyl)acryloyl polycarbonates according to the invention with related unique properties. This crosslinking may be carried out by for instance a reaction with a difunctional reagent, such as di-thiol, a di-amine, and an aminothiol. Examples of suitable difunctional reagents are 1,6-hexanedithiol, ethylene diamine, and 2-mercaptoethylamine. In the alternative or in addition crosslinking may also take place by photo-crosslinking or by gamma irradiation. It is also possible to crosslink the (alkyl)acryloyl polycarbonates of the invention after grafting with an unsaturated monomer, such as (meth)acrylic acid and (meth)acrylic esters.

The polymers or (alkyl)acryloyl polycarbonates comprise unsaturated pendant groups. These groups may be used for crosslinking, but these groups may also be used for functionalizing the polymers or (alkyl)acryloyl polycarbonates of the invention with any suitable functional group by a reaction with the unsaturated groups in the polymer chain. Obviously, the pendant unsaturated groups may on the one hand be used for functionalization and on the other for crosslinking. Both these modifications of the polymer or (alkyl)acryloyl polycarbonate chains may be carried out before or after the creation of the biodevice. In other words the functionalized and/or crosslinked (alkyl)acryloyl polycarbonate according to the invention may be formed into the biodevice of the invention. In the alternative the polymer or (alkyl)acryloyl polycarbonate of the invention may first be attached or formed into the biodevice and afterwards functionalized and/or crosslinked.

Thus, according to a preferred embodiment of the invention the polymer or (alkyl)acryloyl polycarbonate is functionalized by a reaction with a difunctional ligand that is reactive with the unsaturated pendant groups of the (alkyl)acryloyl polycarbonate of the present invention. Such difunctional ligand is preferably a thiol-containing functional ligand and/or an amine-containing functional ligand. Preferred examples of the thiol-containing functional ligand are 2-mercaptoethanol, 3-mercaptopropanoic acid, cysteamine, cysteine, mercapto saccharide, PEG-SH, and arginine-glycine-aspartic acid-cysteine (RGDC) peptide. A preferred example of the amine-containing functional ligand is 2-amino ethanol. Obviously, any further functional ligand that shows reactivity with the pendant groups of the polymer or (alkyl)acryloyl polycarbonate of the invention can be used as long as the integrity and properties of the polymer or the (alkyl)acryloyl polycarbonate are maintained or maintained at an acceptable level.

As discussed above the polymer or (alkyl)acryloyl polycarbonate of the present invention as such or after modification by crosslinking and/or functionalization may be grafted to provide other or additional properties to the (alkyl)acryloyl polycarbonate. Thereto it is preferred that the (alkyl)acryloyl groups of the (alkyl)acryloyl polyester are grafted with unsaturated monomers.

According to another aspect the invention relates also to the (alkyl)acryloyl polycarbonates of the invention, such as (alkyl)acryloyl polycarbonates, (alkyl)acryloyl polyester carbonates and (alkyl)cryloyl poly ester amide carbonates obtainable by the method according to the invention. These (alkyl)acryloyl polycarbonates may be crosslinked and/or functionalized by any suitable manner. Some examples are (meth)acryloyl polycarbonate, (meth)acryloyl polyester carbonate, (meth)acryloyl polyester amide carbonate; optionally crosslinked and/or grafted. These (alkyl)acryloyl polycarbonates, (alkyl)acryloyl polyester carbonates and (alkyl) acryloyl polyester amide carbonates may be functionalized with a thiol-containing functional ligand and/or an amine-containing functional ligand.

According to a further aspect of the invention the (alkyl) acryloyl polycarbonate may be used in the making of biodevices. A biodevice is a device which is intended to be used in combination with a biological system. Preferably the biodevice is in temporary or continuous contact with the biological system. This means that the biodevice should be compatible with the biological system such that the functioning or the properties of the biological system are not substantially changed or modified other than in an intended manner. The biodevice may be intended for being incorporated or implemented in the biological system, such as the human or animal body, although application in plants is also contemplated. The biodevice may have the form of an implant, such as a stent, a blood vessel, a tissue support, a detection system for a biological molecule, such as a metabolite, an enzyme, antibody or viral particle, or a drug delivery system, such as in combination with drug delivery matrix or coating. These biodevices are to be compatible with the biological system with which they are to be used. Another example of a biodevice of the present invention is a system used for cell or tissue culture in which culture systems polymers, such as the (alkyl)acryloyl polycarbonates, (alkyl)acryloyl polyester carbonates, and (alkyl)acryloyl polyester amide carbonate may form part or the entire confinement of the cells or tissue. Under circumstances it may be required such as for drug delivery systems, tissue supports, wound fibres, webs and cloths, that the biodevice should be biodegradable within or after a certain time period.

The polymers, such as the (alkyl)acryloyl polycarbonates, (alkyl)acryloyl polyester carbonates, and (alkyl)acryloyl polyester amide carbonates can be prepared such directly and/or after functionalization that they impart the biodevice with the required properties in relation to stability, biocompatibility and/or biodegradability.

Accordingly, another aspect of the invention relates to a biodevice, such as a stent, blood vessel, and cell compartment, comprising or have been made using the polymer, such as (alkyl)acryloyl polycarbonate, (alkyl)acryloyl polyester carbonate, and/or (alkyl)acryloyl polyester amide carbonate according to the invention.

Examples of the biodevice of the invention are (alkyl) acryloyl polycarbonates bound to a hydrogel, preferably comprising a biologically active agent, such as an antibody, an enzyme.

The surface of a substrate of a biodevice may be coated with a polymer according to the present invention and subsequently the (alkyl)acryloyl groups of the polymer that are exposed at the surface may be modified to introduce a suitable chemical functionality at the surface, such as for immobilization of a hydrogel or a layer of a water swellable polymer to the surface. Suitable hydrogels or water swellable polymers may be based on dextrans and/or PEO. After immobilization of the hydrogel or water swellable polymer, the (residual) chemical functionality of the hydrogel or water swellable polymer can be used for further surface modification such as the immobilization of bio-active molecules that provide the surface with a specific biological activity. For instance an antibody can be immobilized that provides the surface with for instance a specific cell capturing activity. A further example of a bio-active molecule is a drug. Also combinations of molecules with different bio-activities can be immobilized. For drugs it may be preferred to immobilize the drug in such a way that it is released in a preferably controlled manner after application of the device. Also the polymer of the present invention itself maybe combined with bio-active molecules (preferably a drug) before the polymer is applied as a coating in the first step, with the intension to have the drug released during application of the device. Alternatively, in the first step, a polymer according to the present invention that is already provided/modified with the desired chemical functionality can be used to coat the surface of the biodevice and then directly immobilize the hydrogel or a layer of a water swellable polymer to the surface.

Another alternative is a procedure in which the (alkyl) acryloyl groups that are exposed at the surface after the first coating step are used to initiate grafting of a monomer that results in a hydrogel or water swellable layer on the surface as for example by grafting acrylic acid. The thus introduced carboxylic acid groups may then be used for the immobilization of the bioactive molecules.

In addition, it is noted that the (alkyl)acryloyl polycarbonates of the invention may be used in a mixture with other polymers. Such polymer blends may then be used as for instance described above for the polymers of the invention.

Finally, the invention also relates to the (alkyl)acryloyl polycarbonates of the invention, or obtainable with the method of the invention, and/or their use in making biodevices, and/or in medicine, and to a cyclic (alkyl)acryloyl carbonate having the formula (4):

(4)

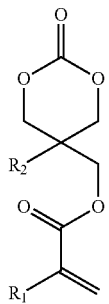

wherein $R_1$ and $R_2$ each independently are hydrogen, methyl or ethyl.

Mentioned and other features of the method of making (alkyl)acryloyl polycarbonates, (alkyl)acryloyl polyester carbonates, and (alkyl)acryloyl polyester amide carbonates, as well as such the (alkyl)acryloyl polycarbonates, and biodevices according to the invention will be further illustrated by several examples and embodiments which are given for information purposes only and are not intended to limit the invention to any extent. In relation to these embodiments reference will be made to the annexed figures of which:

FIG. 1. $^1$H NMR spectra (400 MHz, CDCl$_3$) of AC (A) and MAC (B) monomers;

FIG. 2. $^1$H NMR spectra (300 MHz, CDCl$_3$) of (M)AC copolymers. (A) P(CL-co-AC); (B) P(CL-co-MAC); and (C)P(LA-co-AC);

FIG. 3. $^1$H NMR spectra (300 MHz, CDCl$_3$) of P(CL-co-AC) 8.9% copolymer modified with 2-mercaptoethanol (A), 2-mercaptoethylamine hydrochloride (B), and 3-mercaptopropanoic acid (C);

FIG. 4. $^1$H NMR spectra (300 MHz, DMSO-d$_6$) of P(CL-co-AC) 8.9% copolymer modified with L-cysteine (A) and RGDC peptide (B);

FIG. 5. Contact angle measurements of functional copolymer films; and

FIG. 6. Images (×400) of L929 cells (left panel) and their nuclei stained with Hoechst 33258 (blue, right panel) after 3 d culture on film of P(CL-co-AC)(RGDC)$_{5.2\%}$(OH)$_{3.7\%}$(a), film of P(CL-co-AC) (b); and tissue culture plastic (c).

EXAMPLE 1

Preparation of Acryloyl Carbonate (AC, 4a) and Methacryloyl Carbonate (MAC, 4b)

AC (4a) and MAC (4b) monomers were synthesized in four steps (see scheme 1). The following is an example of synthesis of 4a, in a similar manner 4b is synthesized. To a stirred solution of 1,1,1-tris(hydroxyl methyl)ethane(THME, 24 g, 0.2 mol) and p-toluenesulfonic acid monohydrate (TsOH, 1.2 g, 6.3 mmol) in THF (375 mL) at room temperature was added dropwise benzaldehyde (21.4 mL, 0.21 mol).

After 16 h reaction, the reaction mixture was neutralized with aqueous ammonia, the solvent was evaporated under reduced pressure, and the residues were dissolved in 150 mL of CH$_2$Cl$_2$ and extracted twice with 150 mL of phosphate buffer (pH 7.4). The organic phase was concentrated to yield 39 g (94%) of a colorless powder of a benzylidene acetal (1).

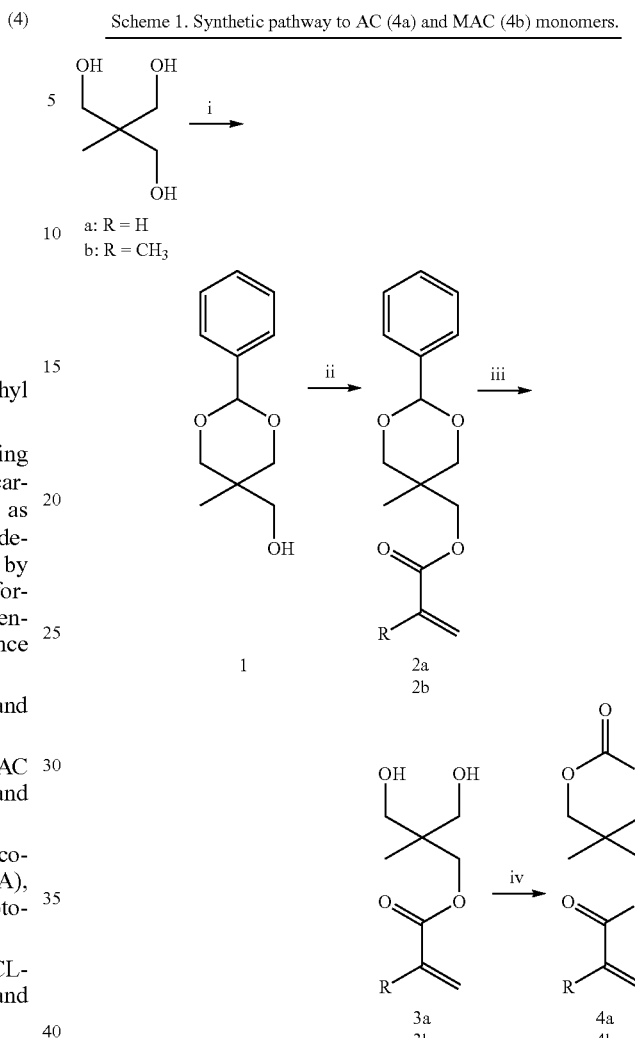

Scheme 1. Synthetic pathway to AC (4a) and MAC (4b) monomers.

Conditions: (i) benzaldehyde, TsOH, THF; (ii) acryloyl chloride (2a) or methacryloyl chloride (2b), (iii) HCl (1.0M), methanol; (iv) ethyl chloroformate, Et$_3$N, THF, 0° C.

To a stirred solution of 1 (10 g, 48 mmol) and Et$_3$N (12 mL, 86.4 mmol) in 150 mL of anhydrous CH$_2$Cl$_2$ at 0° C. was added dropwise acryloyl chloride (5.8 mL, 72 mmol) dissolved in CH$_2$Cl$_2$. After 4 h reaction at 0° C., the reaction mixture was filtered. The filtrate was washed twice with phosphate buffer (pH 7.4) and then concentrated to yield crude 2a. 2a was dissolved in 160 mL of CH$_3$OH/1.0 M HCl (v/v 1/1) and stirred at room temperature for 2 h. The solution pH was then adjusted to 7.0 using 2 M NaOH. The solution was concentrated and extracted with ethyl acetate. The organic phase was concentrated to yield crude product mono-acryloyl THME 3a, which was purified by column chromatography (eluent: ethyl acetate/petroleum ether). Yield: 5.07 g (61%). $^1$H NMR (400 MHz, CDCl$_3$): δ 086 (s, 3H), 2.96 (s, 2H), 3.56 (q, 2H), 4.26 (s, 2H), 5.88-6.42 (m, 3H).

To a stirred solution of 3a (4 g, 22.9 mmol) and ethyl chloroformate (4.6 mL, 48.09 mmol) in dried THF (150 mL) at 0° C. was added dropwise Et$_3$N (7 mL, 50.49 mmol) dissolved in THF. After 4 h reaction at 0° C., the reaction mixture was filtered, and the filtrate was concentrated under reduced pressure. The residues were crystallized in diethyl ether to yield 4a. Yield: 2.94 g (64%). $^1$H NMR (400 MHz, $CDCl_3$): δ 1.14 (s, 3H), 4.17 (d, 2H), 4.19 (s, 2H), 4.33 (d, 2H), 5.91-6.45 (m, 3H), see FIG. 1. Elemental Anal. Calcd. for $C_9H_{12}O_5$: C, 54.00; H, 6.04. Found: C, 53.87; H, 6.06.

In a similar way, 4b was prepared with an overall yield of 40%. $^1$H NMR (400 MHz, $CDCl_3$): δ 1.12 (s, 3H), 1.96 (s, 3H), 4.16 (s, 2H), 4.18 (d, 2H), 4.33 (d, 2H), 5.64 (s, 1H), 6.12 (s, 1H), see FIG. 1. Elemental Anal. Calcd. for $C_{10}H_{14}O_5$: C, 56.07; H, 6.59. Found: C, 56.18; H, 6.52.

EXAMPLE 2

Direct Synthesis of Cyclic Carbonate Monomer (without Protection)

The AC monomer 4a is synthesized in two steps, that is, without protection and deprotection. Typically, to a solution of THME (35 g, 0.29 mol) in 700 mL of THF at room temperature was added 20 mL of $Et_3N$ (0.15 mol). The solution was cooled to 0° C. A solution of acryloyl chloride (10 mL, 0.12 mol) in THF was added dropwise. After 4 h reaction at 0° C., the solvent was removed by rotary evaporator. The residues were dissolved in phosphate buffer (pH 7.4), and were twice extracted with ethyl acetate. The organic phase was concentrated and purified by column chromatography (eluent: ethyl acetate/petroleum ether=1/1 v/v) to obtain product 3a. Yield: 8.2 g (39.2%). $^1$H NMR (400 MHz, $CDCl_3$): δ 0.86 (s, 3H), 2.96 (s, 2H), 3.56 (q, 2H), 4.26 (s, 2H), 5.88-6.42 (m, 3H).

To a stirred solution of 3a (8.2 g, 46.95 mmol) and ethyl chloroformate (9.5 mL, 99.32 mmol) in dried THF (350 mL) at 0° C. was added dropwise a solution of $Et_3N$ (16.1 mL, 115.9 mmol) in THF. After 4 h reaction at 0° C., the reaction mixture was filtered, and the filtrate was concentrated under reduced pressure. The residues were crystallized in diethyl ether to yield 4a. Yield: 5.75 g (62%). $^1$H NMR (400 MHz, $CDCl_3$): δ 1.14 (s, 3H), 4.17 (d, 2H), 4.19 (s, 2H), 4.33 (d, 2H), 5.91-6.45 (m, 3H).

In a similar manner can be produced the MAC (4b).

EXAMPLE 3

Ring-Opening Copolymerization of poly(CL-co-AC), poly(CL-co-MAC), poly(LA-co-AC), poly(LA-co-MAC), and poly(TMC-co-AC)

The polymerization was carried out in toluene at 110° C. using isopropanol as an initiator and $Sn(Oct)_2$ as a catalyst. The synthesis of P(CL-co-AC) 8.9% is as follows (see also scheme 2). In a glove-box under a nitrogen atmosphere, to a stirred solution of ε-CL (1.539 g, 13.5 mmol) and AC (0.3 g, 1.5 mmol) in toluene (20 mL) was quickly added isopropanol stock solution (0.26 mL, 0.75 M) and $Sn(Oct)_2$ stock solution (1 mL, 0.1 M). The monomer to initiator mole ratio was set at 80/1, and the monomer feed was 10 mol %. The reaction vessel was sealed and placed in an oil-bath thermostated at 110° C. After 24 h polymerization, the reaction was terminated by two drops of acetic acid. The resulting polymer P(CL-co-AC) 8.9% was isolated by precipitation in cold diethylether and dried in vacuo at room temperature.

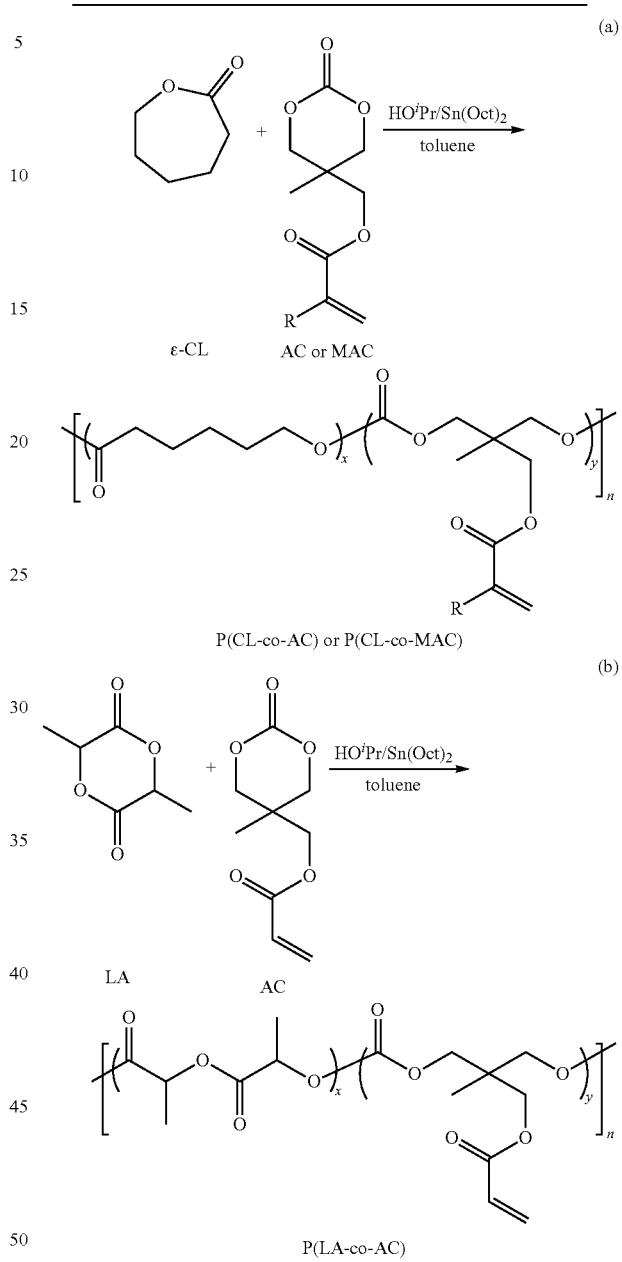

Scheme 2. Ring-opening copolymerization of (M)AC with ε-Cl and LA.

(a) ε-CL and (M)AC; (b) LA and AC.

$^1$H NMR spectra were recorded on the Unity Inova 400 and NMR system (Varian) operating at 400 and 300 MHz, respectively. $CDCl_3$ and DMSO-$d_6$ were used as solvents and the chemical shifts were calibrated against residual solvent signals. The molecular weight and polydispersity of the copolymer was determined by a Waters 1515 gel permeation chromatograph (GPC) instrument equipped with two linear PLgel columns (500 Å and Mixed-C) following a guard column and a differential refractive-index detector. The measurements were performed using THF as the eluent at a flow rate of 1.0 mL/min at 30° C. and a series of narrow polystyrene standards for the calibration of the columns. Contact angle was determined by POWEREACH Instrument (Micaren, JC2000C/X).

In a similar manner using MAC instead of MA and/or LA instead of ε-CL the copolymers poly(CL-co-MAC), poly(LA-co-AC), poly(LA-co-MAC) have been produced (see also scheme 2).

Furthermore, another (alkyl)acryloyl polyester was synthesized using trimethylene carbonate (TMC) as the second monomer.

The copolymerization of (M)AC with ε-CL, LA, and/or TMC went smoothly affording copolymers with controlled molecular weights ($M_n$) in the range of 8000 to 20,000 (depended on the method) and moderate polydispersities (PDI=1.26-1.60), see Table 1.

TABLE 1

Synthesis of (meth)acryloyl functionalized biodegradable copolymers by ring-opening copolymerization

| Entry | Copolymer | $F^a$% | $F^b$% | theo.$^c$ | $M_n \times 10^{-3}$ $^1$H NMR$^d$ | GPC$^e$ | PDI GPC$^e$ |
|---|---|---|---|---|---|---|---|
| 1 | P(CL-co-AC) 8.9% | 10 | 8.9 | 9.5 | 9.7 | 12.2 | 1.41 |
| 2 | P(LA-co-AC) 6.1% | 10 | 6.1 | 9.9 | 9.9 | 14.0 | 1.26 |
| 3 | P(CL-co-MAC) 7.6% | 10 | 7.6 | 9.4 | 11.2 | 18.5 | 1.27 |
| 4 | P(CL-co-AC) 16% | 20 | 16 | 9.9 | 11.5 | 19.3 | 1.44 |
| 5 | P(TMC-co-AC) | 10 | 8.3 | 8.9 | 8.2 | 10.9 | 1.60 |

$^a$Molar fraction of (M)AC monomer in feed;
$^b$Molar fraction of (M)AC units in the resulting copolymer determined by $^1$H NMR;
$^c$Theoretic molecular weight calculated based on monomer-to-initiator ratio and monomer conversions (determined by $^1$H NMR);
$^d$Estimated by $^1$H NMR end-group analysis;
$^e$Determined by GPC (eluent: THF, flow rate: 1.0 mL/min, standards: polystyrene).

It is noted that $^1$H NMR displayed clear resonances at δ 5.6-6.4 attributable to intact acryloyl protons (FIGS. 2A and 2B) and at δ 5.6-6.1 assignable to intact methacryloyl protons (FIG. 2C) for copolymers of AC and MAC, respectively.

The composition of the copolymers could be determined by comparing integrals of signals of (meth)acryloyl protons with those of PCL methylene protons at δ 2.30, PLA methine proton at δ 5.16, and PTMC methylene protons at δ 2.05. Notably, P(CL-co-AC) chains contained 8.9 mol. % of AC units, close to the feed of 10 mol. % (Table 1, Entry 1). This copolymer is accordingly denoted as P(CL-co-AC) 8.9%. The copolymerization of AC with LA yielded copolymers with 6.1 mol. % AC (Table 1, Entry 2).

The capability of copolymerization with LA renders these functional cyclic carbonate monomers highly attractive for diverse biomedical applications. Similarly, copolymerization of MAC with ε-CL afforded P(CL-co-MAC) containing 7.6 mol. % MAC (Table 1, Entry 3). At a higher feeding ratio of 20 mol. % AC monomer, P(CL-co-AC) with 16 mol. % AC units was obtained (Table 1, Entry 4). The copolymerization of TMC and AC at a molar feed ratio of 10 mol. % AC yielded a copolymer containing 8.3 mol. % AC units (Table 1, Entry 5) Moreover, $^1$H NMR end-group analysis revealed that all copolymers had molecular weights close to the theoretical values (Table 1). It is evident, therefore, that both (meth)acryloyl functionality and molecular weights of these functional copolymers could be readily controlled.

EXAMPLE 4

Synthesis of (Alkyl)Acryloyl Polycarbonate Block Copolymers

EXAMPLE 4A

Synthesis of PEG$_{5k}$-P(TMC$_{157}$-co-AC$_6$)

The ring-opening polymerization was carried out in CH$_2$Cl$_2$ at 40° C. using zinc bis[bis(trimethylsilyl)amide] as the catalyst and methoxy PEG ($M_n$=5000) as a polymerization initiator. In the glove-box under a nitrogen atmosphere to a stirring solution of PEG (0.28 g, 0.056 mmol), AC (0.1 g, 0.5 mmol) and TMC (0.9 g, 8.82 mmol) in CH$_2$Cl$_2$ (10 mL) was quickly added zinc bis[bis(trimethylsilyl)amide] (11 mg, 0.03 mmol). The reaction vessel was sealed and placed in an oil-bath thermostated at 40° C. The polymerization was allowed to proceed with magnetic stirring for 1 day. The resulting polymer was isolated by twice precipitation from cold diethylether and dried under vacuum at room temperature. $^1$H NMR (400 MHz, CDCl$_3$) for PEG$_{5k}$-P(TMC$_{157}$-co-AC$_6$) copolymer: δ 1.06 (s, —CCH$_3$), 2.05 (m, —CH$_2$CH$_2$CH$_2$—), 3.38 (s, PEG-OCH$_3$), 3.64 (s, —CH$_2$OCH$_2$—), 4.11 (s, —OCH$_2$CCH$_2$O—, —CH$_2$OCOCH═CH$_2$), 4.24 (t, —CH$_2$CH$_2$CH$_2$—), 5.6-6.4 (m, CH$_2$═CH—). GPC characterization (eluent: THF, flow rate: 1.0 mL/min, standards: polystyrene): $M_n$=24900, PDI=1.54.

EXAMPLE 4B

Synthesis of PEG$_{5k}$-PAC$_{1.4k}$-PDLLA$_{4.8k}$ Triblock Copolymer

The ring-opening polymerization was carried out in two steps using zinc bis[bis(trimethylsilyl)amide] as the catalyst and methoxy PEG ($M_n$=5000) as an initiator. In the glove-box under a nitrogen atmosphere to a stirring solution of PEG (0.34 g, 0.068 mmol) and AC (0.15 g, 0.75 mmol) in CH$_2$Cl$_2$ (3 mL) was quickly added zinc bis[bis(trimethylsilyl)amide] (18 mg, 0.05 mmol). After 2 days reaction at r.t. in the glove-box, DLLA (0.3 g, 2.08 mmol) dissolved in CH$_2$Cl$_2$ (2 mL) was added into the reaction solution, then the reaction vessel was sealed and placed in an oil-bath thermostated at 40° C. The polymerization was allowed to proceed with magnetic stirring for another 2 days. The resulting polymer was isolated by precipitation from cold diethylether and dried under vacuum at room temperature. $^1$H NMR (400 MHz, CDCl$_3$) for PEG$_{5k}$-PAC$_{1.4k}$-PDLLA$_{4.8k}$ copolymer: δ 1.06 (s, —CCH$_3$), 1.58 (d, CH$_3$CHCO—), 3.38 (s, PEG-OCH$_3$), 3.64 (s, —CH$_2$OCH$_2$—), 4.10 (s, —OCH$_2$CCH$_2$O—, —CH$_2$OCOCH═CH$_2$), 5.20 (m, —CH(CH$_3$)CO—), 5.6-6.4 (m, CH$_2$═CH—). GPC characterization (eluent: THF, flow rate: 1.0 mL/min, standards: polystyrene): $M_n$=14300, PDI=1.17.

EXAMPLE 5

Functionalization of the (Alkyl)Acryloyl Polycarbonates

The (alkyl)acryloyl polycarbonates were functionalized by an addition reaction on the pendant (alkyl)acryloyl groups, such as by a Michael addition reaction. Michael addition reaction was carried out in DMF at room temperature under a nitrogen atmosphere. Exemplified is the functionalization of P(CL-co-AC) 8.9%. P(CL-co-AC) 8.9%, was functionalized with thiol-containing molecules (R—SH: 2-mercaptoethanol, 2-mercaptoethylamine hydrochloride, 3-mercaptopropanoic acid or L-cysteine). The reaction was carried out in DMF at a mole ratio AC/R—SH/pyridine of 1/10/10 at room temperature, see Scheme 3. The reaction was allowed to proceed for 2 to 3 d. The resulting functional polymers were isolated by precipitation from cold diethylether/ethanol and dried in vacuo at room temperature.

For modification with RGDC, P(CL-co-AC) 8.9%, RGDC and pyridine were reacted in DMF at a mole ratio AC/RGDC/pyridine of 1/1/10 at room temperature, see Scheme 3. The reaction was allowed to proceed for 7 d. Then, 2-mercaptoethanol (five-fold relative to AC units) was added to react with the remaining AC groups. The reaction was continued for another 2 d. The resulting RGD functionalized polymer was isolated by precipitation from cold ethanol and dried in vacuo at room temperature.

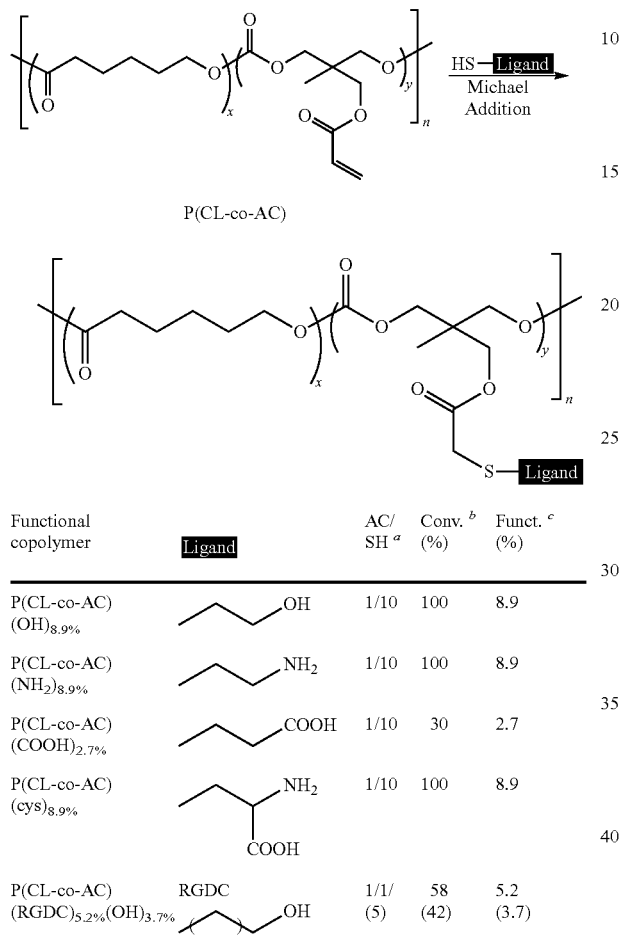

Scheme 3. Modifications of P(CL-co-AC) 8.9% copolymer with thiol-containing molecules by Michael addition reaction.

[a] AC/SH mole ratio in feed;
[b] conversion of AC units determined by $^1$H NMR;
[c] functionality defined as mole percentage of functional ligands.

As a result of the functionalization reaction $^1$H NMR revealed complete disappearance of peaks assignable to acryloyl groups and occurrence of new signals corresponding to 2-mercaptoethanol and cysteamine moieties, respectively (FIGS. 3A and 3B), indicating 100% functionalization with 2-mercaptoethanol and cysteamine (denoted as P(CL-co-AC) (OH)$_{8.9\%}$ and P(CL-co-AC) (NH$_2$)$_{8.9\%}$, respectively). The functionalization of P(CL-co-AC) 8.9% with 3-mercaptopropanoic acid yielded a 30% conversion of acryloyl groups, to give P(CL-co-AC) (COOH)$_{2.7\%}$ (FIG. 3C). Noticeable, the GPC curves of all modified copolymers remain unimodal with similar PDI to the parent copolymer, indicating minimal degradation during modification.

Michael addition reaction allowed post-polymerization functionalization under conditions that are mild. Accordingly, delicate bioactive molecules including peptides and proteins may functionalize the (alkyl)acryloyl polyesters through their cysteine moieties. The functionalization of P(CL-co-AC) 8.9% with cysteine or with RGDC peptide showed 100% functionalization under the same reaction conditions as described above to afford P(CL-co-AC) (cys)$_{8.9\%}$, as shown by $^1$H NMR (FIG. 4A). The modification of P(LA-co-AC) 6.1% with cysteine also resulted in quantitative functionalization, yielding P(LA-co-AC) (cys)$_{6.1\%}$. The reaction with RGDC peptide was slightly different, in which AC/RGDC/pyridine mole ratio was set at 1/1/10 and after 7 d reaction 2-mercaptoethanol (5-fold relative to AC units) was added to consume the remaining AC groups. Markedly, $^1$H NMR showed that RGDC has successfully been conjugated to the copolymer with 58% RGDC functionalization (FIG. 4B). The remaining AC units were completely derivatized with 2-mercaptoethanol, yielding P(CL-co-AC) (RGDC)$_{5.2\%}$ (OH)$_{3.7\%}$.

EXAMPLE 6

Biodevice—Tissue Culture System

Preparation of Functional Copolymer Films

Thin films were prepared by casting functionalized copolymer solutions in DMF (0.5 wt %) on microscope slides. The films on the slides were dried by placing in a desiccator for 18 h followed by vacuum-drying for 3 days to remove DMF thoroughly. The resulting films were uniform. The static contact angle measurements (using POWEREACH Instrument) demonstrated that P(CL-co-AC) 8.9% modified with 2-mercaptoethanol, cysteamine, cysteine and RGDC, all displayed increased hydrophilicity as compared to the parent copolymer (FIG. 5). The negligible change of hydrophilicity of P(CL-co-AC) 8.9% modified with 3-mercaptopropanoic acid is most likely due to its moderate degree of functionalization. In a similar way, increased hydrophilicity was also observed for cysteine-modified P(LA-co-AC) 6.1% copolymer (FIG. 5), though decrease of contact angle was to a less extent than cysteine-modified P(CL-co-AC) 8.9%.

Cell Culture Study

The above-prepared functionalized copolymer coated microscope slides were placed in a 24-well tissue culture plate. The whole plate was sterilized by radiation prior to use. L929 fibroblasts were seeded at a density of 5×10$^5$ cell/well in a humidified 5% CO$_2$ atmosphere at 37° C. The culture media was replaced each day. After 3 d culture, the media was removed, and the cells were rinsed two times with fresh media prior to the microscope observation. To visualize cell nuclei by fluorescence microscopy, the cells were washed three times with PBS, fixed with 4% paraformaldehyde, and stained with Hoechst 33258 (KeyGEN, China). The cells were observed under an inverted microscope (Nikon Eclipse 80i Microscope equipped with a DS camera cable).

FIG. 6 shows images of cells after 3 day culture. The cell nuclei were stained with Hoechst 33258 (blue). It is interesting to note that films of RGD modified P(CL-co-AC) supported better cell adhesion and growth as compared to those of the parent copolymer as well as the tissue culture plastic. Importantly, the morphology of the cells as well as their nuclei on RGD modified copolymer films appeared to be typical of fibroblasts in native tissues. Furthermore, unlike films of P(CL-co-AC) and tissue culture plastic, unhealthy round-shaped cells were practically absent for the functionalized films of P(CL-co-AC) (RGDC)$_{5.2\%}$ (OH)$_{3.7\%}$. These results indicated that activities of RGDC peptides maintained over the mild Michael addition reaction. RGD peptides have been widely applied to stimulate cell adhesion (e.g. in tissue engineering applications). These (alkyl)acryloyl cyclic carbonate monomers provide a new entry for functionalization by anchoring peptides and proteins on synthetic biodegradable polymers for diverse biomedical devices and applications including medical devices, tissue engineering, and drug delivery systems.

The invention claimed is:

1. A method for making a modified (alkyl)acryloyl polymer, comprising the following steps:
   (a) subjecting a cyclic(alkyl)acryloyl carbonate to ring opening polymerization, thereby forming a polymer which bears at least one pendant (alkyl)acryloyl group, wherein said-cyclic(alkyl)acryloyl carbonate is of formula (4):

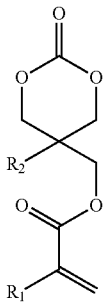

(4)

wherein $R_1$ and $R_2$ each independently are hydrogen, methyl or ethyl;
   (b) modifying the at least one (alkyl)acryloyl group of the polymer by a process which comprises reacting the (alkyl)acryloyl group with a functional ligand; and
   said functional ligand is a thiol-bearing ligand or an amine-containing ligand.

2. The method as claimed in claim 1, wherein the cyclic (alkyl)acryloyl carbonate is prepared by (i) (alkyl)acrylation of 1,1,1-tris(hydroxyl methyl)alkane or (ii) (alkyl)acrylation of aryl acetal protected 1,1,1-tris(hydroxyl methyl)alkane, deprotection, and ring-formation.

3. The method according to claim 1, wherein said thiol-bearing ligand is selected from the group consisting of 2-mercaptoethanol, 3-mercaptopropanoic acid, cysteamine, and cysteine.

4. The method according to claim 1, wherein said functional ligand is selected from the group consisting of 1,6-hexanedithiol, ethylene diamine, and 2-mercaptoethylamine.

* * * * *